United States Patent
Radicke

(10) Patent No.: US 10,441,228 B2
(45) Date of Patent: Oct. 15, 2019

(54) BREAST EXAMINATION APPARATUS AND COMPRESSION PLATE FOR A BREAST EXAMINATION APPARATUS

(71) Applicant: SIEMENS AKTIENGESELLSCHAFT, Munich (DE)

(72) Inventor: Marcus Radicke, Veitsbronn (DE)

(73) Assignee: Siemens Aktiengesellschaft, Munich (DE)

( * ) Notice: Subject to any disclaimer, the term of this patent is extended or adjusted under 35 U.S.C. 154(b) by 121 days.

(21) Appl. No.: 15/051,864

(22) Filed: Feb. 24, 2016

(65) Prior Publication Data

US 2016/0242709 A1   Aug. 25, 2016

(30) Foreign Application Priority Data

Feb. 24, 2015   (DE) .................. 10 2015 203 310

(51) Int. Cl.
*A61B 6/04* (2006.01)
*A61B 6/00* (2006.01)
*A61B 6/02* (2006.01)

(52) U.S. Cl.
CPC .......... *A61B 6/0414* (2013.01); *A61B 6/025* (2013.01); *A61B 6/502* (2013.01); *A61B 6/547* (2013.01)

(58) Field of Classification Search
CPC ....... A61B 6/025; A61B 6/0414; A61B 6/502; A61B 6/547; A61B 10/0233; A61B 17/3403; A61B 2562/168; A61B 5/0004; A61B 5/1451; A61B 5/14532; A61B 5/4839; A61B 6/06; A61B 6/102; A61B 8/0825; A61B 8/0841; A61B 8/4209; A61B 8/4281; A61B 90/17; A61B 6/4417;
(Continued)

(56) References Cited

U.S. PATENT DOCUMENTS 4,573,180 A * 2/1986 Summ .................... A61B 6/502
                                                         378/180
5,820,552 A * 10/1998 Crosby ................ A61B 8/0825
                                                         600/407
(Continued)

FOREIGN PATENT DOCUMENTS

CN       101247761 A       8/2008
DE       19837264 A1 *    3/2000    ............ A61B 8/0825
(Continued)

OTHER PUBLICATIONS

Yang et al., "Fundamentals of Electromechanical System Design—Chapter 2: Design of mechatronic mechanical systems", General Advanced 12th Five-year Plan Textbook, published Jun. 30, 2014, pp. 8-11—English translation.
(Continued)

*Primary Examiner* — Irakli Kiknadze
(74) *Attorney, Agent, or Firm* — Laurence Greenberg; Werner Stemer; Ralph Locher

(57) ABSTRACT

An imaging breast examination apparatus for medical examination of a breast includes an insertable compression plate for compressing the breast. An electric motor which is disposed outside the compression plate in the breast examination apparatus serves to generate a rotation movement. A mechanical interface transmits the rotation movement of the electric motor to the compression plate.

14 Claims, 2 Drawing Sheets

(58) Field of Classification Search
CPC ......... A61B 8/4416; A61B 3/11; A61B 6/032;
A61B 6/5217; A61B 6/5205; A61B
6/463; A61B 6/4233; A61B 6/4258; A61B
6/467; A61B 6/542; A61B 6/544; A61B
6/545; A61B 6/461; A61B 6/466; A61B
8/406; A61B 6/5247; A61B 6/0435; A61B
8/523
USPC .................................................. 378/37, 208
See application file for complete search history.

(56) References Cited

U.S. PATENT DOCUMENTS

| | | | | |
|---|---|---|---|---|
| 6,157,697 | A * | 12/2000 | Mertelmeier | A61B 5/0536 378/37 |
| 7,453,979 | B2 * | 11/2008 | Sendai | A61B 6/025 378/23 |
| 8,611,491 | B2 | 12/2013 | Holler et al. | |
| 9,855,014 | B2 * | 1/2018 | Davis | A61B 6/025 |
| 2003/0181801 | A1 | 9/2003 | Lasser et al. | |
| 2003/0198315 | A1 | 10/2003 | Andreasson et al. | |
| 2007/0274438 | A1 | 11/2007 | Hyvarinen et al. | |
| 2009/0234229 | A1 * | 9/2009 | Mikami | A61B 6/0414 600/445 |
| 2011/0087098 | A1 | 4/2011 | Fischer et al. | |
| 2011/0311024 | A1 * | 12/2011 | Koehler | A61B 6/484 378/37 |
| 2014/0093034 | A1 * | 4/2014 | Takata | A61B 6/544 378/37 |

FOREIGN PATENT DOCUMENTS

| | | | | |
|---|---|---|---|---|
| EP | 0775467 | A1 | 5/1997 | |
| JP | 2009285345 | A | 12/2009 | |
| JP | 2014068885 | A | 4/2014 | |
| WO | WO 0189380 | A2 * | 11/2001 | ........... A61B 5/0536 |

OTHER PUBLICATIONS

Helber Gregor, "Mechatronics Charting Manual", published Dec. 31, 2014, pp. 272-273—English translation.

* cited by examiner

BREAST EXAMINATION APPARATUS AND COMPRESSION PLATE FOR A BREAST EXAMINATION APPARATUS

CROSS-REFERENCE TO RELATED APPLICATION

This application claims the priority, under 35 U.S.C. § 119, of German Patent Application DE 10 2015 203 310.4, filed Feb. 24, 2015; the prior application is herewith incorporated by reference in its entirety.

BACKGROUND OF THE INVENTION

Field of the Invention

The present invention relates to an imaging breast examination apparatus for medical examination of a breast, and a compression plate for a breast examination apparatus.

Mammography apparatuses and tomosynthesis apparatuses are becoming ever more complex and, in addition to a normal X-ray examination of the breast, also offer biopsies or ultrasound examinations. For that purpose, compression plates are provided with additional features. A motor control and an electric motor are installed in the compression plates, which makes the compression plates heavy. Moreover, the handling of the compression plates is made complicated by the attachment of additional cables. In addition, the component parts are not mechanically protected in the best way possible and are susceptible to electromagnetic interference as a result of poor shielding.

Japanese Patent Application JP 2009/285345 relates to a compression plate for pressing a breast against a photographic plate.

Japanese Patent Application JP 2014/68885 relates to a compression plate with a pressing area lying opposite an imaging surface of an image panel.

SUMMARY OF THE INVENTION

It is accordingly an object of the invention to provide a breast examination apparatus and a compression plate for a breast examination apparatus, which overcome the hereinafore-mentioned disadvantages of the heretofore-known devices of this general type, which can be easily handled and which have a light weight.

With the foregoing and other objects in view there is provided, in accordance with the invention, an imaging breast examination apparatus for medical examination of a breast, including an insertable compression plate for compressing the breast, an electric motor, which is disposed outside the compression plate in the breast examination apparatus and serves to generate a rotation movement, and a mechanical interface for transmitting the rotation movement of the electric motor to the compression plate. This affords the technical advantage, for example, that the weight of the compression plate is reduced. Moreover, there is less technical outlay, since the electric motor and the control system of the electric motor can be used for a plurality of compression plates.

In an advantageous embodiment of the breast examination apparatus, the compression plate includes a toothed belt, which is coupled to the mechanical interface in order to convert the rotation movement into a movement within the compression plate. This affords the technical advantage, for example, that the motor power can be converted in a simple way to a desired movement.

In another advantageous embodiment of the breast examination apparatus, the compression plate includes a toothed wheel, which is coupled to the mechanical interface in order to convert the rotation movement into a movement within the compression plate. This likewise affords the technical advantage, for example, that the motor power can be converted in a simple way to a desired movement.

In a further advantageous embodiment of the breast examination apparatus, the compression plate includes a drive rod for transmitting the rotation movement. This affords the technical advantage, for example, that the rotation movement can be transmitted into the interior of the compression plate.

In an added advantageous embodiment of the breast examination apparatus, the drive rod protrudes from the mechanical interface. This affords the technical advantage, for example, that the drive rod can be coupled to the breast examination apparatus in a simple way.

In an additional advantageous embodiment of the breast examination apparatus, the compression plate includes a first drive rod for transmitting the rotation movement and a second drive rod for transmitting a further rotation movement. This affords the technical advantage, for example, that two independent movements of the compression plate can be realized.

In yet another advantageous embodiment of the breast examination apparatus, the compression plate includes a gear for switching the rotation movement in different directions. This affords the technical advantage, for example, that, depending on the position of the gear, a single transmitted rotation movement can be converted to different directions.

In yet a further advantageous embodiment of the breast examination apparatus, the compression plate includes a fastening device for a transducer. This affords the technical advantage, for example, that the compression plate or paddle can be configured without cable attachments and that the compression plate or paddle is lighter and easier to store.

In yet an added advantageous embodiment of the breast examination apparatus, the fastening device is disposed in such a way that a fastened transducer blocks a release of the compression plate from the breast examination apparatus. This affords the technical advantage, for example, that a removal of the compression plate with the transducer attached is prevented.

In yet an additional advantageous embodiment of the breast examination apparatus, the fastening device includes a dovetail guide for guiding the transducer. This affords the technical advantage, for example, that the transducer can be easily inserted into the fastening device.

In again another advantageous embodiment of the breast examination apparatus, the fastening device includes a magnet or a locking device for fastening the transducer. This affords the technical advantage, for example, that the transducer can be fastened quickly.

In again a further advantageous embodiment of the breast examination apparatus, the fastening device includes an electrical data interface for transmitting the data from the transducer. This affords the technical advantage, for example, that the data of the transducer can be transmitted after the fastening of the compression plate to the transducer or of the transducer to the compression plate.

In again an added advantageous embodiment of the breast examination apparatus, the compression plate includes an electrical data interface for transmitting data to the breast examination apparatus. This affords the technical advantage, for example, that data of additional sensors in the compression plate can be transmitted.

In again an additional advantageous embodiment of the breast examination apparatus, the data interface is configured in such a way that it connects up when the compression plate is inserted into the breast examination apparatus. This affords the technical advantage, for example, that the data interface is ready for use directly after the insertion of the compression plate.

In still another advantageous embodiment of the breast examination apparatus, the compression plate includes a coding for automatically detecting the type of the compression plate. This affords the technical advantage, for example, that different programs can be offered to the user through the detection of the compression plate.

With the objects of the invention in view there is concomitantly provided, as a second aspect, a compression plate for a breast examination apparatus for compressing the breast in a medical examination, including a mechanical interface for transmitting the rotation movement of an electric motor to the compression plate. In this way, the same technical advantages are afforded as by the breast examination apparatus according to the first aspect.

Other features which are considered as characteristic for the invention are set forth in the appended claims.

Although the invention is illustrated and described herein as embodied in a breast examination apparatus and a compression plate for a breast examination apparatus, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

The following detailed description of the figures uses the drawings to discuss illustrative embodiments, which are not to be construed as restrictive, along with the features and further advantages thereof.

DETAILED DESCRIPTION OF THE INVENTION

Figure 1:
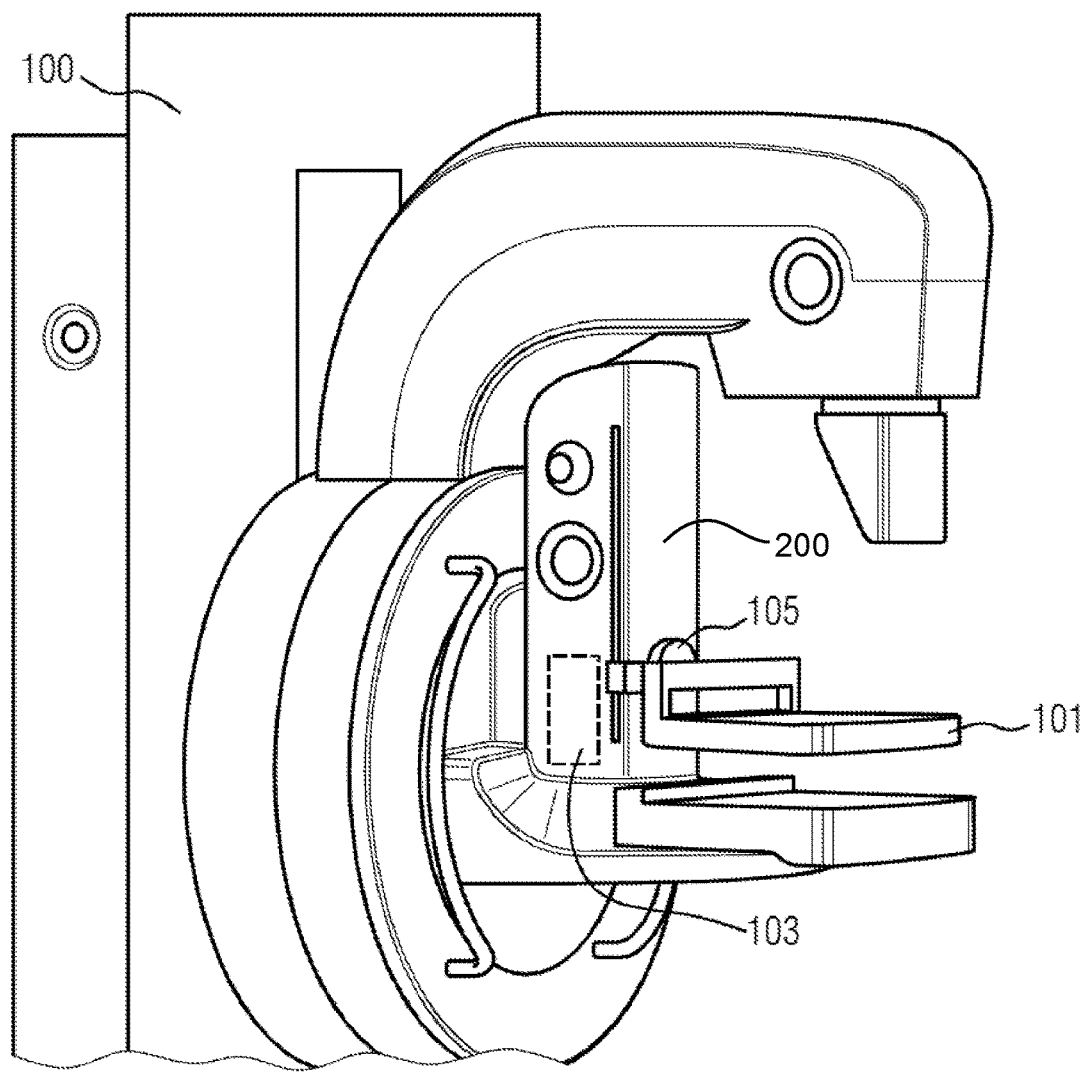
FIG. 1 is a diagrammatic, perspective view of a breast examination apparatus.

Referring now to the figures of the drawings in detail and first, particularly, to FIG. 1 thereof, there is seen a view of a breast examination apparatus 100, for example a mammography apparatus or tomosynthesis apparatus. The breast examination apparatus 100 serves for the medical examination of a breast. For this purpose, the breast is compressed by an exchangeable compression plate 101 during the examination. The compression plate 101 is manually insertable into the breast examination apparatus 100.

The breast examination apparatus 100 includes an electric motor 103, which is installed in the breast examination apparatus 100 outside the compression plate 101, for example a stepped motor with a motor control system. The electric motor 103 serves to generate a rotation movement.

The compression plate 101 includes a mechanical interface 105 for transmitting the rotation movement of the electric motor 103 to the compression plate 101. Therefore, in the compression plate 101, there is only a mechanical transmission of the rotation movement, which can be converted into the specifically required movement by using toothed belts or toothed wheels.

An automatic identification of the compression plate 101 by using an optical code can offer the user various programs, for example the start of an automatic ultrasound examination or a biopsy of a 3D coordinate to be set.

Figure 2:
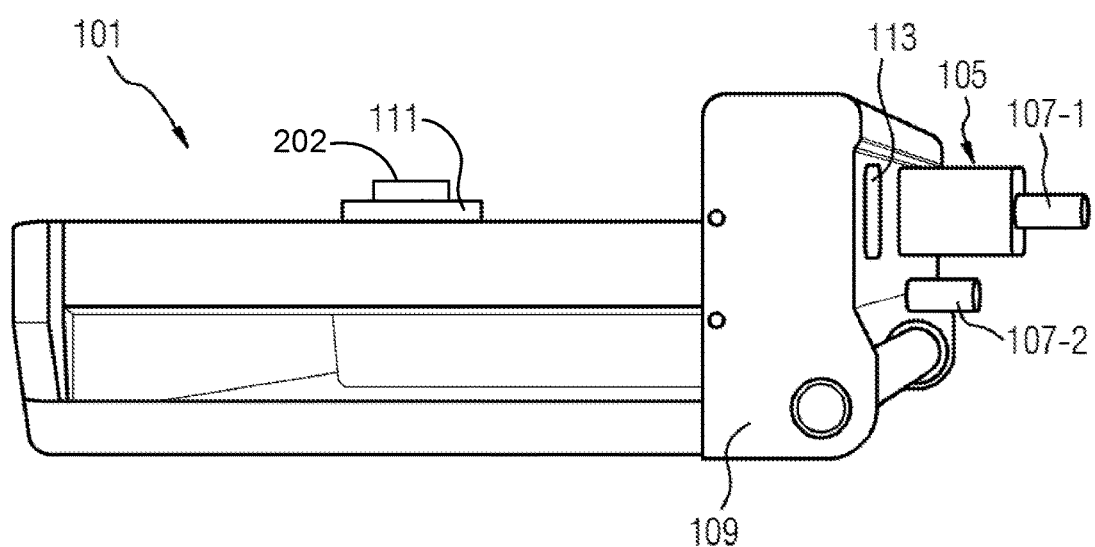
FIG. 2 is a perspective view of a compression plate.

FIG. 2 shows a view of a compression plate 101. A movement coupling is configured in such a way that a rotatable drive rod 107-1 and/or 107-2 is provided in the mechanical interface 105 of the compression plate 101. The drive rod 107-1 and 107-2 protrudes from the rear face of the compression plate 101.

When the compression plate 101 is latched into the breast examination apparatus 100, the drive rod 107-1 and 107-2 is then coupled automatically to the electric motor 103. A coupling piece for coupling the drive rod 107-1 and 107-2 is located, for example, behind a flap in the housing 200 of the breast examination apparatus. The flap opens automatically upon insertion of the drive rod 107-1 and 107-2, in such a way that a connection can be produced.

Two drive rods 107-1 and 107-2 can be fitted at the same time into the compression plate 101 for precise two-dimensional movements. Moreover, a gear 109 can be fitted in the compression plate 101 in such a way that, with the drive rod not rotating, and by using a longitudinal movement of the drive rod, for example in the anterior/posterior direction, a toothed wheel to be driven within the compression plate 101 is changed. A different movement of the compression plate 101 takes place depending on the driven toothed wheel.

Moreover, each two-dimensional coordinate on the compression plate or paddle can also be realized with only one drive rod 107-1 or 107-2 without a gear. If the starting point is always in a corner of the compression plate 101, only two movement directions are needed in order to control each desired point on the compression plate 101.

The compression plate 101 can include a fastening device 111 for a transducer 202. The transducer 202 serves for ultrasound examination of the breast and is located on or in the breast examination apparatus 100. If necessary, the transducer 202 can be pulled out through an automatic roll-up cable and can be manually secured on the fastening device 111 of the compression plate 101. The fastening device 111 includes, for example, a dovetail guide for guiding the transducer during the insertion, which guide includes an electric magnet or a clip/screw.

The fastening device 111 can be disposed in such a way that a secured transducer blocks a release of the compression plate 101 from the breast examination apparatus 100. In this way, the compression plate 101 is locked, in such a way that there is no possibility of uncoupling from the breast examination apparatus 100 until the transducer is again located in its base.

Alternatively, a cordless transducer can be used which is electrically charged in a base in the breast examination apparatus 100. The recorded data of the cable-free transducer can be stored on a temporary basis in the transducer until they are read out in the base station of the transducer in the breast examination apparatus 100.

The fastening device 111 can include an electrical data interface and a current supply for transmitting the data from the transducer. In this way, the transducer can also be connected electrically to the breast examination apparatus 100 when latched into the compression plate 101.

Furthermore, the compression plate 101 includes an electrical data interface 113 for transmitting data to the breast examination apparatus 100. In this way, an electrical interface between the breast examination apparatus 100 and the compression plate 101 can be formed. It is not just the data of the transducer that can be transmitted through this data interface 113, but also the data of additional sensors, of a mood light, of a biopsy and/or ultrasound control.

The data interface 113 is configured in such a way that it connects up when the compression plate 101 is inserted into the breast examination apparatus 100. The electrical connection is produced by latching the compression plate 101 on the breast examination apparatus. An assignment of the electrical pins of the data interface 113 can be coupled to add-on systems of the breast examination apparatus 100 and configured according to the requirements of the hospital.

Weight reduction is achieved by using the exchangeable compression plate 101. The weight reduction is technically advantageous since the compression plate 101 is frequently exchanged. Moreover, there is less technical outlay, since the electric motor and the control system inside the breast examination apparatus can be used for different compression plates 101. The breast examination apparatus 100 has no exposed cables in the area of the compression plate 101. Moreover, possibilities exist for expanding the breast examination apparatus according to the requirements of the hospital.

All of the features explained and illustrated in conjunction with individual embodiments of the invention may be provided in various combinations in the subject matter according to the invention in order to simultaneously provide the advantageous effects thereof.

The scope of protection of the present invention is specified by the appended claims and is not restricted by the features explained in the description or shown in the drawing.

The invention claimed is:

1. An imaging breast examination apparatus for medical examination of a breast, the breast examination apparatus comprising:
    a housing for housing the breast examination apparatus;
    an insertable compression plate for compressing the breast; and
    an electric motor disposed outside said compression plate in the breast examination apparatus and serving to generate a rotation movement;
    said compression plate including a rear face having an electrical data interface attached thereto, said rear face having a mechanical interface for transmitting said rotation movement of said electric motor to said compression plate;
    said compression plate including a drive rod for transmitting said rotation movement, said drive rod protruding from said rear face of said compression plate; and
    said electric motor disposed inside said housing.

2. The breast examination apparatus according to claim 1, wherein said drive rod protrudes from said mechanical interface.

3. The breast examination apparatus according to claim 1, wherein said compression plate includes a first drive rod for transmitting said rotation movement and a second drive rod for transmitting a further rotation movement.

4. The breast examination apparatus according to claim 1, wherein said compression plate includes a fastening device for a transducer.

5. The breast examination apparatus according to claim 4, wherein said fastening device includes a magnet or a locking device for fastening the transducer.

6. The breast examination apparatus according to claim 4, wherein said fastening device includes at least one of an electrical data interface for transmitting data from the transducer or a current supply for supplying the transducer with electrical energy.

7. The breast examination apparatus according to claim 1, wherein said electrical data interface is configured for transmitting data to the breast examination apparatus.

8. The breast examination apparatus according to claim 7, wherein said electrical data interface is configured to connect when said compression plate is inserted into the breast examination apparatus.

9. The breast examination apparatus according to claim 1, wherein said electric motor is not disposed on said compression plate.

10. The breast examination apparatus according to claim 1, wherein said mechanical interface is formed by at least one rotatable drive rod.

11. The breast examination apparatus according to claim 1, wherein said compression plate includes a longitudinally extending face defining a top or a bottom face of said compression plate, said longitudinally extending face has a transducer attached thereto, and said electrical data interface attached to said rear face provides data from said transducer attached to said longitudinally extending face.

12. A compression plate for a breast examination apparatus for compressing the breast in a medical examination, the compression plate comprising:
    a rear face having an electrical data interface attached thereto, said rear face having a mechanical interface for transmitting a rotation movement of an electric motor to the compression plate; and
    a drive rod for transmitting said rotation movement, said drive rod protruding from said rear face;
    wherein the electric motor is not disposed on the compression plate.

13. The compression plate according to claim 12, wherein said mechanical interface is formed by at least one rotatable drive rod.

14. The compression plate according to claim 12, further comprising: a longitudinally extending face defining a top or a bottom face of said compression plate, said longitudinally extending face having a transducer attached thereto, and said electrical data interface attached to said rear face providing data from said transducer attached to said longitudinally extending face.

* * * * *